(12) United States Patent
Lopez et al.

(10) Patent No.: US 7,337,751 B2
(45) Date of Patent: Mar. 4, 2008

(54) VETERINARY GONIOMETER FOR TESTING OF ANIMAL LEG JOINTS

(75) Inventors: Mandi J. Lopez, McFarland, WI (US); Orrin D. Lokken, Madison, WI (US); Mark D. Markel, Middleton, WI (US); William W. D. Hagquist, DeForest, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 215 days.

(21) Appl. No.: 10/903,116

(22) Filed: Jul. 29, 2004

(65) Prior Publication Data

US 2005/0034684 A1 Feb. 17, 2005

Related U.S. Application Data

(60) Provisional application No. 60/491,652, filed on Jul. 31, 2003.

(51) Int. Cl.
*A01K 15/04* (2006.01)
(52) U.S. Cl. .......................... 119/755; 33/512; 600/592
(58) Field of Classification Search ................. 33/174, 33/511, 512; 119/755, 756; 128/740, 774, 128/779, 782
See application file for complete search history.

(56) References Cited

U.S. PATENT DOCUMENTS

| | | | |
|---|---|---|---|
| 4,306,571 A * | 12/1981 | McLeod, Jr. ................. | 600/595 |
| 4,583,555 A * | 4/1986 | Malcom et al. .............. | 600/595 |
| 4,649,934 A | 3/1987 | Fraser et al. | |
| 4,913,163 A * | 4/1990 | Roger et al. ................. | 600/595 |
| 4,969,471 A * | 11/1990 | Daniel et al. ................ | 600/587 |
| 4,969,895 A | 11/1990 | McLeod et al. | |
| 5,014,719 A * | 5/1991 | McLeod ....................... | 600/587 |
| 5,168,634 A * | 12/1992 | Misevich ....................... | 33/515 |
| 5,348,025 A * | 9/1994 | Wolfe et al. ................. | 600/595 |
| D352,111 S | 11/1994 | Watkins | |
| 5,383,474 A * | 1/1995 | Akhter et al. ................ | 600/595 |
| 5,460,596 A * | 10/1995 | Brady ............................ | 601/35 |
| 5,870,832 A * | 2/1999 | Slocum ......................... | 33/511 |
| 5,935,086 A | 8/1999 | Beacon et al. | |
| 5,957,869 A | 9/1999 | Caruso et al. | |
| 6,419,645 B1 * | 7/2002 | Rijke ............................ | 600/587 |
| 6,983,547 B2 * | 1/2006 | Fleming et al. .............. | 33/503 |
| 2003/0048455 A1 * | 3/2003 | Fleming et al. .............. | 356/500 |

* cited by examiner

*Primary Examiner*—Teri Pham Luu
*Assistant Examiner*—Valentina Xavier
(74) *Attorney, Agent, or Firm*—Craig A. Fieschko, Esq.; DeWitt Ross & Stevens S.C.

(57) ABSTRACT

A goniometer (also sometimes referred to as an arthrometer, fleximeter, or pronometer) for measuring the range of motion of an animal knee includes an anchor platform to which an animal's upper leg (femur) may be affixed, and a mobile platform to which the animal's lower leg (shin and tibia) may be affixed so that the upper and lower leg are situated along a common axis. The mobile platform is preferably movable in two degrees of freedom (translational and rotational) about the anchor platform so that the relative motion of the platforms causes the upper and lower leg to move about the intermediate knee joint. A force transducer (such as a spring scale) and/or a torque transducer (such as a common torque wrench) may be used to obtain measurements of the laxity of the knee joint.

61 Claims, 1 Drawing Sheet

VETERINARY GONIOMETER FOR TESTING OF ANIMAL LEG JOINTS

CROSS-REFERENCE TO RELATED APPLICATIONS

This application claims priority under 35 USC §119(e) to U.S. Provisional Patent Application 60/491,652 filed 31 Jul. 2003, the entirety of which is incorporated by reference herein.

FIELD OF THE INVENTION

This document concerns an invention relating generally to veterinary diagnostic devices for determining characteristics of animal musculoskeletal systems, and more specifically to goniometers for measuring laxity in animal leg joints.

BACKGROUND OF THE INVENTION

As in humans, animal knee joints do not include interlocking bones, and instead the femur (thigh bone) and tibia (shin bone) are simply joined with several ligaments—in particular, the cruciate ligaments, which are given that name because they cross from side to side when extending from femur to tibia. Thus, as in humans, animals are also prone to knee injuries owing to damage to their cruciate ligaments. Such injuries, which at best cause diminished mobility and at worst are crippling, are painful for pets and are very distressing for pet owners. In cases where the pet is a companion animal (e.g., a seeing-eye dog), an injury can even have a drastic effect on the pet owner's lifestyle.

Cruciate ligament injuries can be partial tears (disruptions) or complete tears (ruptures). A disruption, while painful, may allow the animal to use the leg, though generally with a limp. However, the joint is still partially unstable: as the animal walks, the femur will slide backwardly over the tibia and generate wear on the joint cartilage, eventually leading to arthritis and greater pain. Additionally, disruptions can grow over time into ruptures. If a cruciate ligament is ruptured, the joint will become entirely unstable because the tibia will no longer be pivotably affixed to the femur, and the animal's ability to walk on the affected leg may be greatly hindered. Disruptions can often be addressed prophylactically via the use of braces and the like, or by surgery. However, a complete rupture can only be addressed by surgery, and recovery is difficult, with arthritis almost invariably developing owing to joint damage.

Since the effects of cruciate ligament injuries can be minimized if they are detected early—as disruptions rather than ruptures—it would be extremely useful to have some means of determining the extent of a ligament injury, whereby the appropriate prophylactic measures can be prescribed before joint damage grows too severe.

SUMMARY OF THE INVENTION

The invention, which is defined by the claims set out at the end of this document, is directed to a goniometer (also known in the literature as an arthrometer, fleximeter, or pronometer) for measuring the range of motion of an animal knee. To give the reader a basic understanding of some of the advantageous features of the invention, following is a brief summary of preferred versions of the goniometer. As this is merely a summary, it should be understood that more details regarding the goniometer may be found in the Detailed Description set forth elsewhere in this document. The claims set forth at the end of this document then define the various versions of the invention in which exclusive rights are secured. To enhance the reader's understanding, the following summary will reference corresponding elements depicted in the accompanying FIGS. 1 and 2.

A veterinary goniometer 100 includes a mobile platform 120 which moves with respect to an adjacent anchor platform 112 so that an animal leg may be affixed to the platforms and the characteristics of its knee joint may be determined. The anchor platform 112 bears upper leg mounting means 116 for affixing an animal's upper leg to the anchor platform 112, with the animal's upper leg then being oriented along an anchored leg axis. The mobile platform 120 similarly bears a lower leg mounting means 122 for affixing an animal's lower leg to the mobile platform 120. By moving the mobile platform 120 with respect to the anchor platform 112, the lower leg is moved with respect to the upper leg about the joint, with the amount of force (or torque) required to effect such motion providing an indication of the degree of laxity in the joint. A plate mount 166 adapted to receive radiographic film 164 is preferably situated beneath the mobile platform 120 so that as the relative positions of the mobile platform 120 and anchor platform 112 are changed to situate the animal's lower and upper leg in different poses, X-rays may be taken of the leg.

The mobile platform 120 is movable in at least one degree of freedom with respect to the anchor platform 112, with preferred arrangements being that the mobile platform 120 is translatable in a testing direction oriented perpendicular to the anchored leg axis (i.e., perpendicular to the animal's upper leg), and/or pivotable about a pivot axis oriented parallel to the anchored leg axis and spaced from the mobile platform 120 on which the leg rests (e.g., so that the pivot axis rests along the anchored leg axis). If the mobile platform 120 is also (or alternatively) translatable, a force transducer 148 is engaged between the anchor platform 112 and mobile platform 120 to provide an indication of the force required to translate the mobile platform 120 with respect to the anchor platform 112 when the animal's leg is mounted thereon. As a result, a veterinarian may determine the force required to generate a given degree of translational joint displacement, with these parameters being important measures of the condition of the animal's leg joint. Where the mobile platform 120 is pivotable, a torque transducer is usefully provided so that the torque required to generate a given amount of twist between the upper and lower leg may be determined, with these parameters also being important measures of joint health. In this case, a preferred arrangement is to situate a connector 156 on the mobile platform 120 at a location spaced from the lower leg mounting means and situated along the pivot axis, with the connector 156 being adapted for the removable connection of a torque transducer (such as a common torque wrench).

It is useful to allow the mobile platform 120 to move both translationally and pivotably in the manner described above so that an animal's leg can be tested for joint translation and twist during the same testing session, in the same device. Where the goniometer 100 allows both modes of motion, a preferred configuration is to provide a goniometer base 102 to which the anchor platform 112 is fixed, and then provide the mobile platform 120 on a series of raised struts 128 which descend from the sides of the mobile platform 120 and which have their strut bases translatably affixed to the goniometer base 102, as by having them ride in the testing direction within slots or on rails 142 on the goniometer base 102. The mobile platform 120 can then be pivotably mounted to the struts 128 by defining curved slots 138 or other curved paths on the struts 128, and having arms 134 extend from the sides of the mobile platform 120 to ride along these paths. With appropriately defined slots/paths on the translating struts 128, the mobile platform 120 can be made pivotable about the anchored leg axis.

Further advantages, features, and objects of the invention will be apparent from the following detailed description of the invention in conjunction with the associated drawings.

DETAILED DESCRIPTION OF PREFERRED VERSIONS OF THE INVENTION

Figure 1:
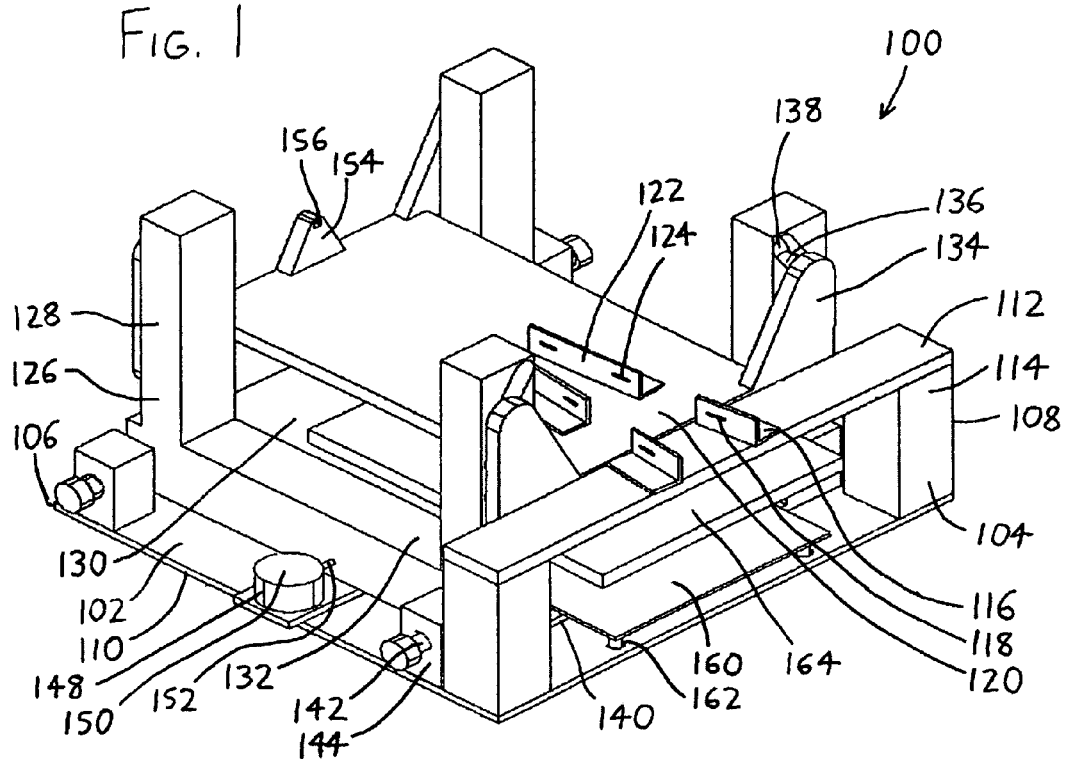
FIG. 1 is a front perspective view of a preferred version of the goniometer, showing its right and front sides 108 and 110.

In FIG. 1, an exemplary goniometer is depicted generally by the reference numeral 100. The goniometer 100 includes a goniometer base 102 suitable for placement on a standard veterinary examination room table, i.e., it has a relatively small footprint, preferably measuring no more than 2-3 feet along any side. The goniometer 100 has a front side 104 at which the animal is located when the device is in use, an opposing rear side 106, and opposing right and left sides 108 and 110.

Figure 2:
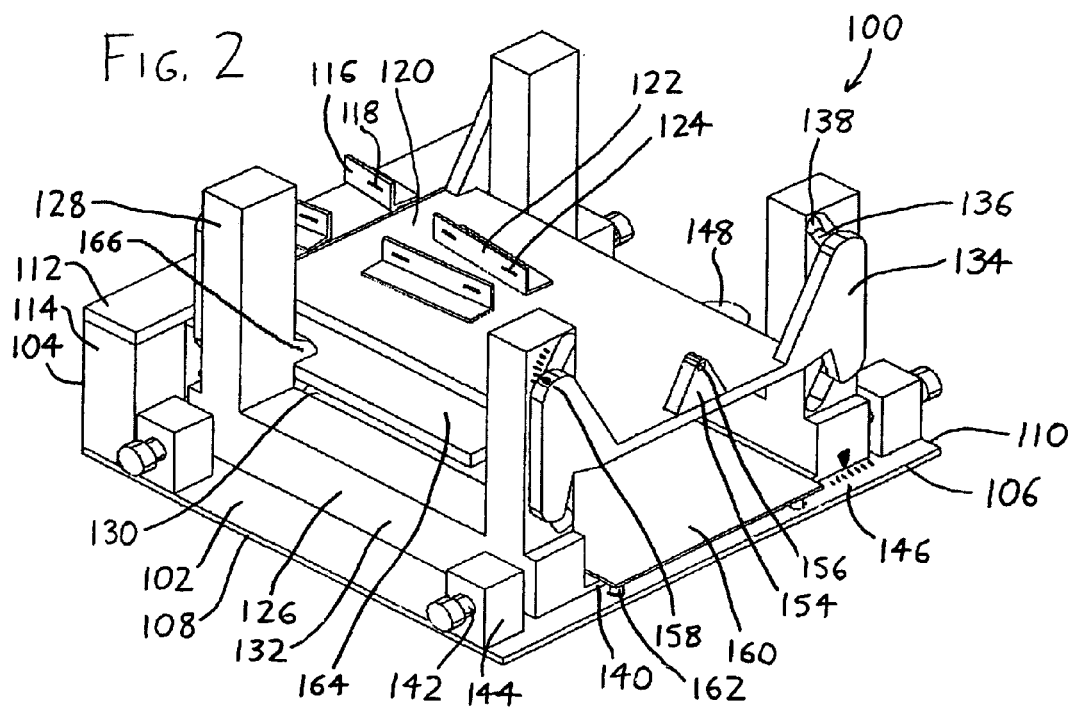
FIG. 2 is a rear perspective view of the goniometer of FIG. 1, showing its left and rear sides 110 and 106.

At the front side 104 of the goniometer 100, an anchor platform 112 is immovably affixed above the goniometer base 102 by a pair of opposing legs 114 bridging the base 102 and anchor platform 112. The anchor platform 112 is intended to hold an animal's upper leg (thigh and femur) immobile as the animal lies on its side adjacent the goniometer 100 so that the relative movement of the lower leg (shin and tibia) can be evaluated. Thus, the anchor platform 112 preferably includes some means for affixing the animal's upper leg to the anchor platform 102, and such an upper leg mounting means is illustrated in FIGS. 1 and 2 as a pair of opposing stops 116 between which the thigh of an animal may be inserted. Strap slots 118 defined in the slots 116 may receive a pair of opposing straps (not shown), e.g., in the form of a strip of fabric having hook-and-loop fasteners at its opposing ends, so that the thigh may be strapped to the anchor platform 112 to be held immobile between the stops 116. Thus, an animal may lie on its side on an examination table with one leg situated on the anchor platform 112 of the goniometer 100, and with its opposite leg situated in the space between the anchor platform 112 and the goniometer base 102 as discussed below.

A mobile platform 120 is then situated next to the anchor platform 112, with the mobile platform 120 preferably being movable in two degrees of freedom about the anchor platform 112: in a direction perpendicular to the axis of the animal's leg when anchored between the stops 116 (i.e., in a direction between the right side 108 and left side 110 of the goniometer 100), and also rotationally, with the mobile platform 120 pivoting about axes parallel to the anchored leg axis (more particularly, about axes parallel to the anchored leg axis and arrayed along a plane distributed between the right side 108 and left side 110 of the goniometer 100). Such motion is exerted on the lower leg (shin and tibia) of an animal, with the lower leg being affixed in a lower leg mounting means affixed to the mobile platform 120. As with the upper leg mounting means on the anchor platform 112, the lower leg mounting means may take a variety of forms, with one exemplary form being depicted in FIGS. 1 and 2 as a pair of stops 122 having strap slots 124, similar to the stops 116 forming the upper leg mounting means. Thus, when the animal's upper leg is affixed within the stops 116 on the anchor platform 112, and the animal's lower leg is affixed within the stops 122 on the mobile platform 120, the mobile platform 120 may be moved with respect to the anchor platform 112 to evaluate the laxity of the leg joint (i.e., the range of motion of the immobilized leg about its joint). Preferably, the upper leg mounting means and lower leg mounting means (i.e., the stops 116 and 122) are oriented such that when the mobile platform 120 is in its datum position with respect to the anchor platform 112—i.e., in a state wherein the mobile platform 120 has yet to be displaced—the animal's upper and lower leg are held fixed with the femur and tibia oriented along a common axis.

The goniometer 100 effects the translational motion by use of the following arrangement. Initially, the mobile platform 120 is situated on a carriage 126 which translates between the right side 108 and left side 110 of the goniometer 100, with the carriage 126 including opposing struts 128 joined to a carriage base 130 at carriage base sides 132. At each of its corners, the mobile platform 120 has protruding wing-like arms 134 extending laterally outwardly towards the right side 108 and left side 110, and these arms 134 bear rod-like followers 136. These followers 136 extend inwardly from the direction of the front side 104 and rear side 106 of the goniometer such that the followers 136 at the front side 104 are in opposing relation with the followers 136 on the rear side 106. The followers 136 ride within curved slots 138 defined in the struts 128, which descend downwardly from the mobile platform 120 to join with the carriage base sides 132. Each carriage base side 132 extends along a portion of the length of the goniometer 100 between its front and rear sides 104 and 106, with the carriage base sides 132 being laterally spaced apart by a carriage base platform 140, with one carriage side 132 proximate the right side 108 and the other proximate the left side 110. The carriage base platform 140, which takes a planar plate-like form, is situated in parallel relationship with the goniometer base 102. The carriage base 130 is then slidably mounted on rails 142, which extend laterally through the carriage base sides 132 between the right and left sides 108 and 110 of the goniometer 100 from blocks 144 extending upwardly from the goniometer base 102. Thus, the carriage 126—including its carriage base platform 140, carriage base sides 132, and struts 128—may laterally translate on the rails 142 to carry the mobile platform 120 between the right and left sides 108 and 110 of the goniometer 100. Such translation need not be significant; a range of 2-4 centimeters of displacement will be sufficient for evaluating the leg joints of most animals. Referring to FIG. 2, ruled lines or other indicia 146 on the carriage 126 (here on the carriage base 130), and/or on the goniometer base 102, can provide an indication of the amount of displacement.

Since it is also useful to obtain a measurement of the force required to effect a given degree of displacement in the animal's leg joint, a force transducer 148 (see primarily FIG. 1) is engaged between the anchor platform 112 and mobile platform 120. A variety of force transducers of different types may be used at different locations on the goniometer 100, and FIGS. 1 and 2 illustrate an exemplary arrangement wherein the force transducer 148 is a simple spring scale having a force-indicating dial 150 affixed to the goniometer base 102, and a spring arm 152 affixed to the carriage 126 at a carriage base side 132. Thus, as the carriage 126 (and thus the mobile platform 120) is translated, displacement of the spring arm 152 generates a force readout at the dial 150.

The rotational motion of the mobile platform 120 is provided to allow evaluation of torsional laxity of the animal's leg joint (i.e., twist between the upper and lower portions of the leg). Such rotational motion is provided by the interaction of the followers 136 of the mobile platform 120 with respect to the curved slots 138 defined in the struts 128. When the curved slots 138 are appropriately defined in the struts 128, the followers 136 will travel within the slots 138 such that the mobile platform 120 pivots about an axis parallel to the axis of the animal's anchored leg. If the mobile platform 120 is not translated out of its datum position with respect to the anchor platform 112, the pivot axis of the mobile platform 120 is parallel to and coincident with the anchored leg axis (the axis along which the anchored animal leg rests). Otherwise, if the mobile platform 120 is translated from its datum position and then pivoted, such pivoting will occur about an axis parallel to and spaced from the anchored leg axis. It is notable that the pivot axis about which the mobile platform 120 pivots is preferably not coincident with the plane of the mobile platform 120, but is rather in a plane coincident with the anchored leg axis, which is spaced slightly above the surface of the mobile platform 120. The slots 112 allow an angular pivoting range of approximately 30 degrees for the mobile platform 120, which is generally sufficient for evaluating the torsional laxity in most cases of animal knee injury.

As with evaluation of displacement between the animal's upper and lower leg, it is useful to have some means of measuring the torque required to effect some degree of twist about the leg joint. Here, a simple and convenient arrangement for measuring torque is provided by situating an ear 154 on the mobile platform 120 at a location spaced from the stops 122, adjacent the rear side 106 of the goniometer 100. The ear 154 bears a connector 156 situated along the pivot axis about which the mobile platform 120 may rotate. The connector 156 is adapted to allow the removable connection of a torque transducer, such as a common torque wrench, so that a torque wrench (or other torque transducer) may be installed and used when desired. In FIGS. 1 and 2, the connector 156 is depicted as a keyway sized and shaped to complementarily receive the driver of a common torque wrench. Thus, the driver of a torque wrench may be inserted within the connector 156, and the torque wrench may be actuated to pivot the mobile platform 120 and provide a measurement of the torque required to pivot the mobile platform 120 with respect to the anchor platform 112. It should be understood that since a variety of torque wrenches having differently-shaped drivers might be used, the connector 156 may take the form of any appropriate female aperture, slot, or other cavity, or any appropriate protruding male terminal, necessary to engage the driver of the selected torque wrench. Alternatively, if a torque transducer other than a torque wrench is used, the connector 156 may take other forms appropriate to provide a removable connection for the transducer; for example, it might accommodate a moment arm to which a spring scale may be affixed so that the force measurement rendered by the spring scale may be converted to a torque measurement. At the same time, indicia 158 on the goniometer 100 (e.g., on the mobile platform arms 134 and the struts 128, see FIG. 2) can provide an indication of the pivot angle resulting from the application of torque.

To provide greater comfort for an animal having its leg affixed to the anchor platform 112 and mobile platform 120, a table 160 is suspended above the goniometer base 102 by legs 162 extending from the goniometer base 102 near the front and rear sides 104 and 106. The table 160 is thereby held immobile with respect to the goniometer base 102, providing a stable platform for the animal's free leg (its leg opposite the leg affixed to the anchor platform 112 and mobile platform 120).

To summarize, when a user wishes to use the goniometer 100 to evaluate the characteristics of an animal's knee joint, the goniometer 100 is placed with its goniometer base 102 on the examination table upon which the animal is laying on its side. One leg is situated on the table 160, and the opposite leg is placed on the anchor platform 112 and mobile platform 120, with the upper leg held within the stops 116 of the anchor platform 112 and the lower leg fixed within the stops 122 of the mobile platform 120 (and with the joint between the upper leg and lower leg preferably situated as closely as possible above the juncture between the mobile platform 120 and anchor platform 112). The mobile platform 120 may then be pushed to have it translate rightwardly or leftwardly between the sides 108 and 110, with the allowable displacement being indicated by the indicia 146 (FIG. 2) and the force required for such displacement being indicated by the force transducer 148 (FIG. 1). Alternatively (or additionally), the mobile platform 120 may be pivoted about its pivot axis by application of torque at the connector 156 (as by applying torque from a torque wrench). Applied torque may simultaneously be measured by the torque wrench, with the pivot angle resulting from the torque being read at indicia 158 (FIG. 2).

It is also useful to incorporate a plate mount 166 for mounting radiographic film 164 below the mobile platform 120, as by providing brackets or receiving notches on the carriage struts 128, so that the animal's leg may be X-rayed in some desired position. If a plate mount 166 is included, radiopaque markers can be incorporated on the mobile platform 120 and/or on other portions of the goniometer 100 so that translational displacements and/or pivot angles might be measurable from the film. Radiographs of the animal's leg can be useful to allow more accurate measurement of displacement and/or twist between the animal's femur and tibia than when such measurements are taken by use of the indicia 146 and 158.

The description set out above is merely of one exemplary preferred version of the invention, and it is contemplated that numerous modifications can be made, and that goniometers in accordance with the invention can be constructed which have significantly different components and appearance. Following are examples of possible modifications.

Initially, while the exemplary goniometer 100 described above uses both pivotal and translational motion, it is possible to construct versions of the invention which only utilize one of these modes of motion. Versions of the invention which incorporate motion along additional or different degrees of freedom are also possible.

The depicted goniometer 100 provides a relatively inexpensive and manually-actuated means for evaluating joint characteristics. However, it is also possible to provide versions of the invention which are partially automated, as by providing pneumatic actuators for translating the carriage 126 and pivoting the mobile platform 120, and automatically providing readouts of force and torque in accordance with the applied pneumatic pressure. Such pneumatic actuation can be effected with use of gas supplies commonly present in veterinary medical facilities. Hydraulic and/or electromechanical actuators (e.g., a servomotor and ball screw) could alternatively or additionally be used.

Note that the anchor platform and mobile platform have been termed "platforms" merely because they serve as members whereupon animal legs may be affixed, and they need not take the form of plates or other members having planar top surfaces; rather, they may take virtually any shape which allows affixation of an animal leg.

A variety of other leg mounting means might be used in lieu of or in addition to the stops 116 and 122, for example, one or more straps, folding shackles, adjustable-diameter cuffs (e.g., pneumatically expanding cuffs), or the like might be directly affixed to the anchor platform 112 without the stops.

The invention is not intended to be limited to the preferred versions of the goniometer described above, but rather is intended to be limited only by the claims set out below. Thus, the invention encompasses all different versions that fall literally or equivalently within the scope of these claims.

What is claimed is:

1. A veterinary goniometer comprising:
   a. an anchor platform having an upper leg mounting means thereon for affixing an animal upper leg to the anchor platform, and wherein an animal upper leg affixed in the leg mounting means is oriented along an anchored leg axis;
   b. a mobile platform adjacent the anchor platform, the mobile platform having a lower leg mounting means thereon for affixing an animal lower leg to the mobile platform, the mobile platform being translatable in a testing direction oriented
      (1) at least substantially perpendicular to the anchored leg axis, and
      (2) at least substantially parallel to the goniometer base; the mobile platform also being pivotable about a pivot axis:
      (3) oriented at least substantially parallel to the anchored leg axis; and
      (4) spaced from the mobile platform;
   c. a force transducer engaged between the anchor platform and mobile platform, the force transducer providing an indication of the force required to translate the mobile platform with respect to the anchor platform;
   d. a goniometer base:
      i. affixed to the anchor platform, and
      ii. about which the mobile platform is restrained to move, with the goniometer base always being spaced from the anchor platform and mobile platform below the anchored leg axis.

2. The veterinary goniometer of claim 1 further comprising a plate mount situated beneath the mobile platform, the plate mount being adapted to receive radiographic film therein.

3. The veterinary goniometer of claim 1 wherein the mobile platform is also pivotable about a pivot axis oriented coincident with or at least substantially parallel to the anchored leg axis.

4. The veterinary goniometer of claim 3 wherein the pivot axis is spaced above the mobile platform.

5. The veterinary goniometer of claim 1 wherein the mobile platform is mounted on struts, the struts descending downwardly from opposing sides of the mobile platform to strut bases, wherein the strut bases are restrained to translate in the testing direction.

6. The veterinary goniometer of claim 5 wherein the mobile platform is pivotably mounted to the struts to pivot about a pivot axis oriented coincident with or parallel to the anchored leg axis.

7. The veterinary goniometer of claim 5 wherein the mobile platform is engaged to each strut to travel along a curved path defined on the strut.

8. The veterinary goniometer of claim 1 wherein the mobile platform has opposing sides with arms extending therefrom, the arms being restrained to travel in curved paths whereby the mobile platform is pivotably mounted about a pivot axis coincident with or parallel to the anchored leg axis.

9. The veterinary goniometer of claim 8 wherein the curved paths are defined on struts which extend downwardly from the mobile platform.

10. The veterinary goniometer of claim 1 further comprising:
    a. a goniometer base, and
    b. struts descending downwardly from opposing sides of the mobile platform to strut bases, wherein the strut bases are restrained to the base to translate thereon in the testing direction.

11. The veterinary goniometer of claim 10 wherein the mobile platform is engaged to the struts to travel along a curved path defined in each strut.

12. The veterinary goniometer of claim 1 further comprising a connector on the mobile platform, the connector being:
    a. adapted for the removable connection of a torque transducer; and
    b. spaced from the lower leg mounting means above the mobile platform.

13. A veterinary goniometer comprising:
    a. an anchor platform having an upper leg mounting means thereon for affixing an animal upper leg to the anchor platform, and wherein an animal upper leg affixed in the leg mounting means is oriented along an anchored leg axis;
    b. a mobile platform adjacent the anchor platform, the mobile platform having a lower leg mounting means thereon for affixing an animal lower leg to the mobile platform, the mobile platform being translatable in a testing direction oriented
       (1) at least substantially perpendicular to the anchored leg axis, and
       (2) at least substantially parallel to the goniometer base; the mobile platform also being pivotable about a pivot axis:
       (3) oriented at least substantially parallel to the anchored leg axis; and
       (4) spaced from the mobile platform;
    c. a plate mount situated beneath the mobile platform, the plate mount being adapted to receive radiographic film therein; d. a goniometer base:
       i. held in fixed relationship to the anchor platform, and
       ii. about which the mobile platform is restrained to move, with the goniometer base always being spaced from the anchor platform and mobile platform below the anchored leg axis.

14. The veterinary goniometer of claim 13 further comprising a force transducer between the anchor platform and mobile platform, the force transducer providing an indication of the force required to translate the mobile platform with respect to the anchor platform.

15. The veterinary goniometer of claim 13 wherein the mobile platform is also pivotable about a pivot axis oriented coincident with or at least substantially parallel to the anchored leg axis.

16. The veterinary goniometer of claim 15 wherein the pivot axis is spaced above the mobile platform.

17. The veterinary goniometer of claim 13 wherein the mobile platform is mounted on struts, the struts extending from opposing sides of the mobile platform to strut bases, wherein the strut bases are restrained to translate in the testing direction.

18. The veterinary goniometer of claim 17 wherein the mobile platform is pivotably mounted to the struts to pivot about a pivot axis coincident with or at least substantially parallel to the anchored leg axis.

19. The veterinary goniometer of claim 17 wherein the mobile platform is engaged to each strut to travel along a curved path defined on the strut.

20. The veterinary goniometer of claim 13 wherein the mobile platform has opposing sides with arms extending therefrom, the arms being engaged to travel in curved paths whereby the mobile platform is pivotably mounted about a pivot axis coincident with or at least substantially parallel to the anchored leg axis.

21. The veterinary goniometer of claim 20 wherein the curved paths are defined on struts which extend downwardly from the mobile platform.

22. The veterinary goniometer of claim 13 further comprising:
   a. a goniometer base, and
   b. struts descending from opposing sides of the mobile platform to strut bases, wherein the strut bases are restrained to the base to translate thereon in the testing direction.

23. The veterinary goniometer of claim 22 wherein the mobile platform travels along a curved path defined in each strut.

24. The veterinary goniometer of claim 13 further comprising a connector fixed to the mobile platform, the connector being:
   a. adapted for the removable connection of a torque transducer; and
   b. spaced from the lower leg mounting means above the mobile platform.

25. A veterinary goniometer comprising:
   a. an anchor platform having an upper leg mounting means thereon for affixing an animal upper leg to the anchor platform, and wherein an animal upper leg affixed in the leg mounting means is oriented along an anchored leg axis;
   b. a mobile platform adjacent the anchor platform, the mobile platform having a lower leg mounting means thereon for affixing an animal lower leg to the mobile platform, the mobile platform being pivotable about a pivot axis:
      (1) oriented at least substantially parallel to the anchored leg axis, and
      (2) spaced from the mobile platform.

26. The veterinary goniometer of claim 16 wherein the mobile platform is also translatable with respect to the anchor platform in a testing direction oriented at least substantially perpendicular to the anchored leg axis.

27. The veterinary goniometer of claim 26 further comprising a force transducer engaged between the anchor platform and mobile platform, the force transducer providing an indication of the force required to translate the mobile platform with respect to the anchor platform.

28. The veterinary goniometer of claim 16 wherein the mobile platform is mounted on struts, the struts extending from opposing sides of the mobile platform to strut bases, wherein the strut bases are restrained to translate in a direction oriented at least substantially perpendicular to the anchored leg axis.

29. The veterinary goniometer of claim 28 wherein the mobile platform is pivotably mounted to the struts, whereby the mobile platform effects the pivoting about the pivot axis.

30. The veterinary goniometer of claim 28 wherein the mobile platform is engaged to each strut to travel along a curved path defined on the strut.

31. The veterinary goniometer of claim 16 wherein the mobile platform has opposing sides with arms extending therefrom, the arms being engaged to travel in curved paths to effect the pivoting of the mobile platform about the pivot axis.

32. The veterinary goniometer of claim 31 wherein the curved paths are defined on struts which extend from the mobile platform.

33. The veterinary goniometer of claim 25 further comprising:
   a. a goniometer base, and
   b. struts descending from opposing sides of the mobile platform to strut bases, wherein the strut bases are translatably restrained to the base.

34. The veterinary goniometer of claim 33 wherein the mobile platform is engaged to the struts to travel along a curved path defined in each strut.

35. The veterinary goniometer of claim 25 further comprising a goniometer base:
   a. anchored in fixed relationship to the anchor platform, and
   b. about which the mobile platform is restrained to move, with the goniometer base always being spaced from the anchor platform and mobile platform.

36. The veterinary goniometer of claim 25 further comprising a connector fixed to the mobile platform, the connector being:
   a. adapted for the removable connection of a torque transducer; and
   b. spaced from the lower leg mounting means adjacent the mobile platform.

37. The veterinary goniometer of claim 25 further comprising a plate mount situated adjacent the mobile platform, the plate mount being adapted to receive radiographic film therein.

38. A veterinary goniometer comprising:
   a. an anchor platform having an upper leg mounting means thereon for affixing an animal upper leg to the anchor platform, and wherein an animal upper leg affixed in the leg mounting means is oriented along an anchored leg axis;
   b. a mobile platform adjacent the anchor platform, the mobile platform being pivotable about a pivot axis oriented coincident with or at least substantially parallel to the anchored leg axis and including:
      (1) a lower leg mounting means thereon for affixing an animal lower leg to the mobile platform; and
      (2) a connector spaced from the lower leg mounting means and situated along the pivot axis, the connector being adapted for the removable connection of a torque transducer.

39. The veterinary goniometer of claim 38 wherein the mobile platform is also translatable with respect to the anchor platform in a testing direction oriented at least substantially perpendicular to the anchored leg axis.

40. The veterinary goniometer of claim 39 further comprising a force transducer engaged between the anchor platform and mobile platform, the force transducer providing an indication of the force required to translate the mobile platform with respect to the anchor platform.

41. The veterinary goniometer of claim 38 wherein the mobile platform is mounted on struts, the struts extending from opposing sides of the mobile platform to strut bases, wherein the strut bases are restrained to translate in a testing direction oriented at least substantially perpendicular to the anchored leg axis.

42. The veterinary goniometer of claim 36 wherein the mobile platform is pivotably mounted to the struts, whereby the mobile platform effects the pivoting about the pivot axis.

43. The veterinary goniometer of claim 36 wherein the mobile platform is engaged to each strut to travel along a curved path defined on the strut.

44. The veterinary goniometer of claim 38 wherein the mobile platform has opposing sides with arms extending therefrom, the arms being engaged to travel in curved paths to effect the pivoting of the mobile platform about the pivot axis.

45. The veterinary goniometer of claim 44 wherein the curved paths are defined on struts which extend from the mobile platform.

46. The veterinary goniometer of claim 38 further comprising:
 a. a goniometer base, and
 b. struts descending from opposing sides of the mobile platform to strut bases, wherein the strut bases are restrained to the base to translate thereon.

47. The veterinary goniometer of claim 46 wherein the mobile platform is engaged to the struts to travel along a curved path defined in each strut.

48. The veterinary goniometer of claim 38 further comprising a goniometer base:
 a. affixed to the anchor platform, and
 b. about which the mobile platform is restrained to move, with the goniometer base always being spaced from the anchor platform, mobile platform, and anchored leg axis.

49. The veterinary goniometer of claim 38 further comprising a plate mount situated adjacent the mobile platform, the plate mount being adapted to receive radiographic film therein.

50. A veterinary goniometer comprising:
 a. an anchor platform having an upper leg mounting means thereon for affixing an animal upper leg to the anchor platform, and wherein an animal upper leg affixed in the leg mounting means is oriented along an anchored leg axis;
 b. a mobile platform adjacent the anchor platform, the mobile platform having a lower leg mounting means thereon for affixing an animal lower leg to the mobile platform, the mobile platform being pivotable about a pivot axis coincident with or at least substantially parallel to the anchored leg axis;
 c. a plate mount situated beneath the mobile platform, the plate mount being adapted to receive radiographic film therein.

51. The veterinary goniometer of claim 50 wherein the mobile platform is also translatable with respect to the anchor platform in a testing direction oriented at least substantially perpendicular to the anchored leg axis.

52. The veterinary goniometer of claim 51 further comprising a force transducer engaged between the anchor platform and mobile platform, the force transducer providing an indication of the force required to translate the mobile platform with respect to the anchor platform.

53. The veterinary goniometer of claim 50 wherein the mobile platform is mounted on struts, the struts extending from opposing sides of the mobile platform to strut bases, wherein the strut bases are restrained to translate in a testing direction oriented at least substantially perpendicular to the anchored leg axis.

54. The veterinary goniometer of claim 53 wherein the mobile platform is pivotably mounted to the struts, whereby the mobile platform effects the pivoting about the pivot axis.

55. The veterinary goniometer of claim 53 wherein the mobile platform is engaged to each strut to travel along a curved path defined on the strut.

56. The veterinary goniometer of claim 50 wherein the mobile platform has opposing sides with arms extending therefrom, the arms being engaged to travel in curved paths to effect the pivoting of the mobile platform about the pivot axis.

57. The veterinary goniometer of claim 56 wherein the curved paths are defined on struts which extend from the mobile platform.

58. The veterinary goniometer of claim 50 further comprising:
 a. a goniometer base, and
 b. struts descending from opposing sides of the mobile platform to strut bases, wherein the strut bases are translatably restrained to the base.

59. The veterinary goniometer of claim 58 wherein the mobile platform is engaged to the struts to travel along a curved path defined in each strut.

60. The veterinary goniometer of claim 50 further comprising a goniometer base:
 a. affixed to the anchor platform, and
 b. about which the mobile platform is restrained to move, with the goniometer base always being spaced from the anchor platform, mobile platform, and anchored leg axis.

61. The veterinary goniometer of claim 50 further comprising a connector fixed to the mobile platform, the connector being:
 a. adapted for the removable connection of a torque transducer; and
 b. spaced from the lower leg mounting means adjacent the mobile platform.

* * * * *